United States Patent [19]

Pierce et al.

[11] Patent Number: 5,693,061
[45] Date of Patent: Dec. 2, 1997

[54] KNOT PULLER INSTRUMENT FOR USE WITH SURGICAL SUTURE IN TYING SURGICAL KNOTS

[76] Inventors: Javin C. Pierce, 4780 Mountain Rd., Stowe, Vt. 05672; Neil J. Maki, 403 Canal St., Thibodaux, La. 70301

[21] Appl. No.: 606,453

[22] Filed: Feb. 23, 1996

[51] Int. Cl.$^6$ ............................................. A61B 17/04
[52] U.S. Cl. ..................... 606/148; 606/139; 606/222; 606/232
[58] Field of Search ........................... 606/148, 139, 606/222, 223

[56] References Cited

U.S. PATENT DOCUMENTS

| | | |
|---|---|---|
| 2,665,692 | 1/1954 | L'Esperance . |
| 2,818,866 | 1/1958 | Thomas . |
| 3,871,379 | 3/1975 | Clarke . |
| 4,481,947 | 11/1984 | Chester . |
| 4,580,560 | 4/1986 | Straith . |
| 5,397,326 | 3/1995 | Mangum . |
| 5,423,836 | 6/1995 | Brown ................................. 606/139 |

FOREIGN PATENT DOCUMENTS

| | | |
|---|---|---|
| 194242 | 3/1967 | U.S.S.R. . |
| 2 181 950 A | 5/1987 | United Kingdom . |

*Primary Examiner*—Michael Buiz
*Assistant Examiner*—Daphna Shai
*Attorney, Agent, or Firm*—Pravel, Hewitt, Kimball & Krieger

[57] ABSTRACT

A knot puller instrument and its method of use with surgical suture aids a surgeon in tying surgical knots. The apparatus includes a main body member that is formed of rigid structural material that can be sterilized such as stainless steel. The body is elongated, having a preferably linear central longitudinal axis, and proximal and distal end portions. The proximal end of the main body provides a handle for gripping. The distal end of the main body is comprised of a pair of spaced apart appendages that are positioned to hold a length of suture therebetween at a transverse concavely shaped bridge portion. A space between the appendages is formed by having one appendage suspended free of the instrument body, connected only to the bridge member. This allows a surgeon to place a length of suture in between the two appendages for engagement by the transverse curved bridge connector. During use, the surgeon simply forces the main body in a desired direction to pull one of the suture free ends away from the knot being formed thus applying tension that helps the surgeon tie a very tight knot.

15 Claims, 5 Drawing Sheets

KNOT PULLER INSTRUMENT FOR USE WITH SURGICAL SUTURE IN TYING SURGICAL KNOTS

BACKGROUND OF THE INVENTION

1. Field of the Invention

The present invention relates to medical instruments and more particularly relates to medical instruments that are useful in assisting a surgeon to tie surgical knots. More particularly, the present invention relates to an improved knot puller surgical instrument for use with surgical suture in tying surgical knots in difficult to reach places such as deep within a body cavity and wherein the main body member of the instrument provides an elongated rigid structural portion that supports a distal end comprised of a pair of spaced apart hook like appendages connected by a transverse curved bridge, one of the hook portions being generally parallel to and spaced from the main body member so that a surgeon can insert suture in a space formed between the instrument body and the spaced apart hook portion.

2. General Background

Surgeons are frequently required to place suture in difficult to reach places. This is a common problem when a surgeon is tying knots in suture that is deep within a body cavity as often occurs during a surgical procedure.

Various types of instruments have developed that assist the surgeon in the tying of knots in such situations.

An example of a recent patent that has issued for an instrument that is used to help the surgeon tie a surgical knot is U.S. Pat. No. 5,397,326 issued to William Mangum and entitled "KNOT PUSHER FOR VIDEOENDOSCOPIC SURGERY". In the Mangum patent, four embodiments of videoendoscopic knot pushers are shown having a main body and first and second fingers whose ends are shaped in a smooth rounded shape to guide a suture and knot into position with a patient's body. The finger members define either a "V" shaped cleft or a smooth walled channel between them for grasping the suture. One embodiment of the invention has a second and third channels for retaining the suture in the fingers even during retraction of the main body. Another embodiment of the invention has a spiral channel formed "upstream" of the finger members for retaining control of the suture even if the suture slips out of the grasp of the channel formed by the first and second finger members.

The Mangum '362 patent references prior art Clark and Clarke-Reich ligators that have cylinders with an essentially circular aperture extending from one end in which the circle has a gap formed in the circumference to admit the suture and to hold the knot at the base of the ligator.

Other patents have issued that relate to forceps instruments that assist a surgeon in suturing. Two such forceps patents are the L'Esperance U.S. Pat. No. 2,665,692 entitled "SUTURING FORCEPS" and the Thomas U.S. Pat. No. 2,818,866 entitled "CORNEOSCLERAL SUTURING FORCEPS". In the L'Esperance U.S. Pat. No. 2,665,692, a suturing forceps includes a pair of elongated parallel arms secured together at one end thereof. Each of the arms is formed at the opposite end with a generally annular jaw having an opening lying upon a longitudinal axis of the arm. The jaws are formed with the plurality of matching serrations on mutually directed faces and extending thereacross.

The Thomas U.S. Pat. No. 2,818,866 discloses a forceps comprising a pair of co-acting tongs for stabilizing the peripheral lip of the cornea adjacent the eyeball during a sewing operating. One of the tongs terminates in a pallet having a transverse offset wall therein forming a transverse ridge. The pallet is operable to support the peripheral lip of the cornea and abutment with the transverse wall thereof and the tines operable to maintain the peripheral lip of the cornea in position in the pallet. This allow a curved needle connected with wound sewing thread to be passed between tines through coaptation margin emerging through the exterior surface of the cornea just beyond the termini of the tines and restricted from penetrating the interior surface of the cornea by the position of the pallet.

The Clarke U.S. Pat. No. 3,871,379 entitled "A LAPAROSCOPY INSTRUMENT AND METHOD FOR SUTURING AND LIGATION". In the Clarke disclosure, there is provided an improved combined laparoscopic needle and forceps comprising an elongated parallelogram type of linkage suitable for insertion through a trocar and having first and second ends, a needle, means for mounting said needle on said first end for movement from a position in substantial alignment with said linkage, which permits it to pass through a trocar, to a position transverse to said linkage, handle means on said second end of said linkage for actuating said linkage to effect movement of said needle, and a forceps construction including jaw means mounted proximate said first end of said needle linkage and being formed from a portion of said linkage and a portion of the holder of the needle. An improved combined laparoscopic forceps, suture guide and cutter comprising an elongated parallelogram type of linkage which is sufficiently slender for passage through a trocar and having first and second ends, jaw means on said first end, and handle means on said second end for actuating said linage to move said jaws, groove means associated with said jaws for receiving a suture to thus act as a suture guide, and cutter means mounted on said jaws for cutting a suture. An improved laparoscopic ligator comprising an elongated stem having first and second ends, a handle at said first end and suture guiding means at said second end, said suture guiding means being of substantially the same cross sectional dimension as said elongated stem for guiding a suture through a trocar. An improved method for performing a surgical operation by laparoscopy comprising the steps of inserting at lest first and second trocars through the body of a patient at spaced locations, inserting a first instrument comprising the above described combined laparoscopic needle and forceps through said first trocar, inserting a second instrument comprising the above described laparoscopic forceps, suture guide and cutter through said second trocar, manipulating said first and second instruments in cooperating relationship with each other in a predetermined area to the central portion of a suture in position, withdrawing one of said instruments to bring the end of the suture outside of the patient's body, tying a knot in the suture outside of the body, and bringing the knot into the desired position by means of said laparoscopic ligator.

A Russian patent 194,242 discloses an opthamological surgical instrument that includes a handle, a blunt hook with a wedge shaped end, differing in that the other end of the handle from the wedge-hook is a "g" shaped hook with a tapered end. This allows loops of sutures to be held without other instruments being needed, thus avoiding the danger of the suture being cut by a scalpel.

A United Kingdom patent GB 2,181,950A discloses a ligature holder which is a supporting ring carrying fixture devices that are secured upon the outer surface of the supporting ring. The fixing devices are made of spring elements which are hooks whose open portion faces in an opposite direction to the surgery field.

The Straith U.S. Pat. No. 4,580,560 discloses a drain inserter that includes an elongated instrument body having a notch at one end defined between two fork portions of the instrument.

An elongated instrument that has a hook at one end portion is disclosed in the Chester U.S. Pat. No. 4,481,947 entitled "ENDOTRACHEAL TUBE RETRACTOR". The endotracheal tube retractor of the Chester patent is used to facilitate endotracheal intubation and endotracheal tube placement. The apparatus is provided with an angled handle and a scoop-shaped blade for engaging and manipulating an endotracheal tube. The retractor may be used in both the direct and blind orotracheal and nasotracheal intubation techniques.

One of the problems with presently available knot tying instruments is that they use a pushing of the instrument against the knot in order to secure it. This can result in large amount of friction between the instrument and the suture and in some situations prevents the tying of a very tight knot. Some instruments that are available tend to consist of an elongated rod that contains a hole in the distal end or face. The opening of the hole is small enough so that the windings tend to butt up against the end/face and are thereby advanced. None of the aforementioned patents allows a surgeon to quickly engage, hold and pull a length of suture during surgery.

SUMMARY OF THE INVENTION

The present invention provides an improved instrument for use in surgery to assist the surgeon in tying surgical knots. The apparatus of the present invention provides an improved knot puller instrument for use with surgical suture. The instrument includes a main body member formed of a rigid structural material that can be sterilized, the body having a proximal end to gripped by the surgeon and a distal end portion to engage the suture.

The distal end portion of the main body has a pair of spaced apart appendages that ate hook shaped, each being positioned to hold a length of suture therebetween. The pair of appendages each have hook portions that include a concavity that faces the instrument body. A transverse curved bridge connector extends between the concavity of each hook portion forming a connection therebetween.

A space is formed between the appendages that define a slot for receiving the length of suture. One of the appendages is entirely spaced away from the instrument body along its length between the bridge connector and a free end portion of the appendage so that the suture can be inserted into the slot at the free end portion by placing the suture in between the free end portion and the instrument body. During use, the hook portions and transverse curved bridge form surfaces that can engage the surgical suture allowing the surgeon to pull a free end of the suture toward the knot to be formed. This allows the surgeon to push on the instrument body with the handle allowing the surgeon to tie the knot by the application of tension to the suture adjacent the knot.

In the one embodiment the present invention relates to a knot puller formed of an elongated rod, the distal end of the rod including: a pulley like structure and a pair of projections originating laterally from the axis of the pulley like structure then parallel to the elongated rod for guiding a retaining the suture, a means for loading suture without an end passing and conversely releasably holding the suture within the pulley like structure.

The present invention also relates to a method of tying a suture or filament with an elongated rod which includes a distal end including a single pulley-like surface, the rotational axis of the pulley-like surface being substantially perpendicular to the axis of the greater portion of the elongated rod. The method includes forming a winding of the filament; locating one proximal filament end around the pulley-like structure (360) degree wraps of suture running from the distal emanation to the winding, to proximally to about a nine (9) o'clock position on pulley like structure, counter clockwise to about a nine (9) o'clock position, then proximal to a user's hand usually holding the more proximally emanating suture from the winding, tensioning both proximal suture ends against the distal end of the pulley like structure, and advancing the rod and thereby pulling the winding through a small space and, at the same time, pulling on the proximal ends of the filament so as to advance the winding.

In one embodiment, the present invention also relates to a knot puller with two appendages emanating from the rotational axis of the pulley like structure to facilitate the engagement of suture, positioning around, and retention to, a pulley like surface, one of these appendages providing a permanent structural fixation of the pulley like structure to the elongated rod, the other providing a means to releasably position the suture(s) around, and maintain contact to, the pulley like structure, its substantial proximal end maintaining close contact with the outer surface of the elongated rod so as to discourage unintended release of the suture and the absolute proximal end of the appendage being slightly chamfered or bent away from the rod so as to form a notch to encourage admission of the suture from the proximal direction, this appendage also being sufficiently yielding enough to act as a spring that can yield under firm admission or exit force of suture, the array of appendages and pulley like structure forming a retaining enclosure for a suture.

The present invention also relates to a method of loading a suture into a retaining enclosure by sliding a suture distally against an elongated rod or shaft until the suture is within the retaining enclosure.

The present invention also relates to a knot puller with a movable structure containing an aperture for receiving sutures or filaments proximal to the winding, having a face for pushing windings against the pulley like surface for the purpose of further tightening the knot.

The present invention also relates to a knot puller with a sharp cutting surface that coacts with an aperture for receiving filaments proximal to the winding that can be manipulated to cut both filaments.

The present invention also relates to a knot puller with a movable structure containing an aperture that is large enough to contain two filaments of suture but is small enough to discourage admission of the winding, and a face large enough to substantially contact the proximal aspect of the winding at the distal limit of its distal-proximal movement, the aperture also having a proximal face that encourages contact of the filaments with the sharp cutting surface near the proximal limit of the structure's distal proximal movement.

The present invention also relates to a knot puller with a movable structure containing an aperture that can admit filaments without end passing that comprises a hook structure, to permit loading of the filaments into the aperture without removal of the tool from within the small space.

The device allows the user to use more styles or knots, specifically square knots, surgeon's knots, whereas the current art of one holed knot pushers are largely limited to advancing slip knot requiring give and take of the two suture ends. The present invention enables users to form ligatures from suture ends of two separate ligatures and or ligatures and anchors. Although some two holed knot pushers can be used to form these types of ligatures, the present invention offers function that is more free to friction than the current art owing to the lack of suture contact with the instrument at the winding, when loaded according to the method described herein.

The present invention also allows for side loading or loading without end passing. The preferred embodiment of the present invention also contains features for two coacting members to compress the winding and a sharpened edge for cutting of the sutures at fixed length. The preferred embodiment has a means of offering visual indication of the level of tension on the sutures.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figures 1, 2, 3, 4, 5:
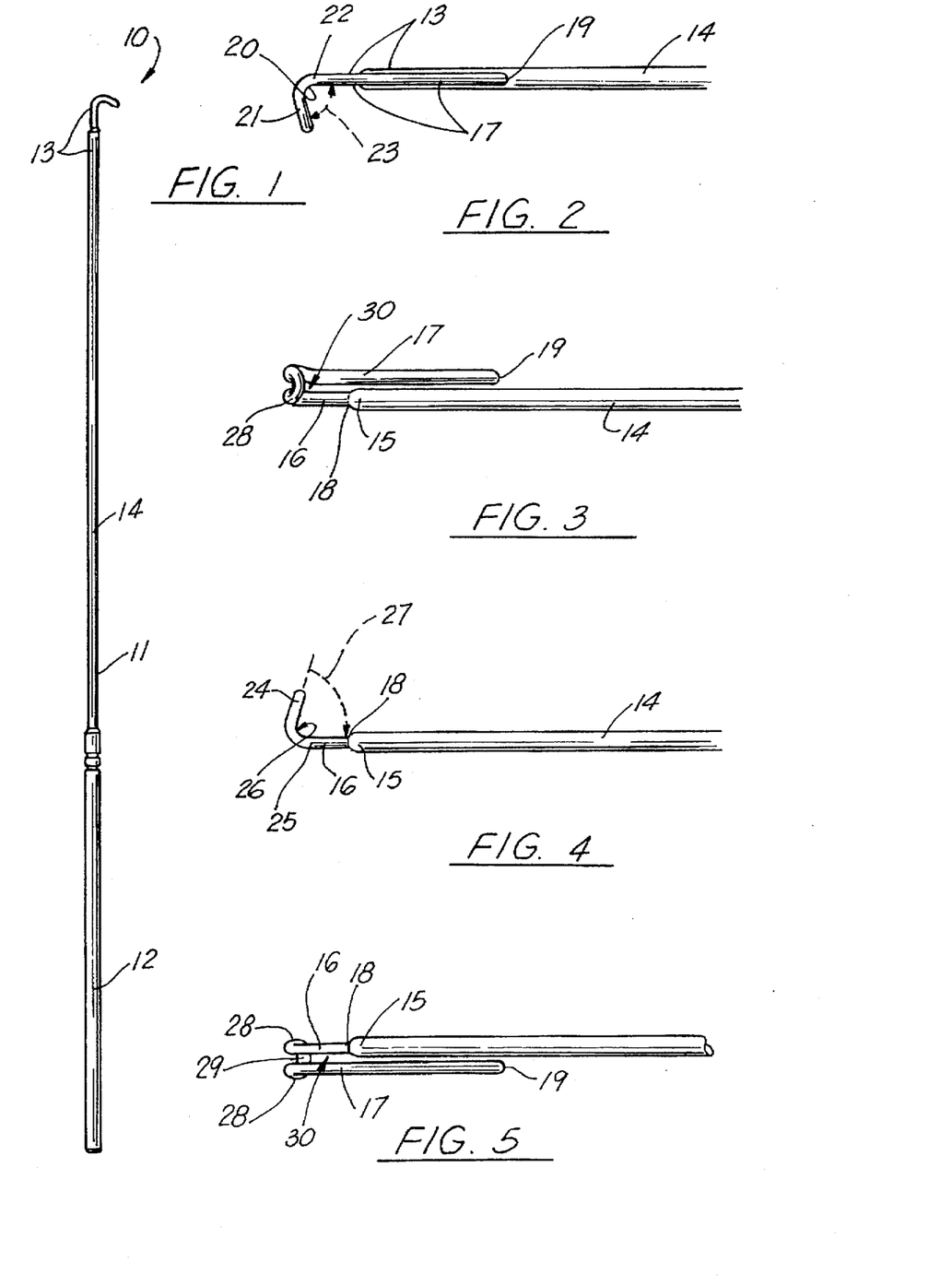
FIG. 1 is a perspective view of the preferred embodiment of the apparatus of the present invention.
FIG. 2 is a fragmentary side view of the preferred embodiment of the apparatus of the present invention.
FIG. 3 is a fragmentary front view of the preferred embodiment of the apparatus of the present invention.
FIG. 4 is a fragmentary side view of the preferred embodiment of the apparatus of the present invention.
FIG. 5 is a fragmentary rear view of the preferred embodiment of the apparatus of the present invention.

FIGS. 1–5 show generally the preferred embodiment of the apparatus of the present invention designated generally by the numeral 10. In FIGS. 1–5, the knot puller instrument 10 includes an elongated instrument body 11 having a proximal end 12 in the form of a handle that can be gripped by the surgeon. The distal end portion 13 of instrument body 11 is connected to handle 12 with an elongated central portion of the instrument in the form of elongated shaft or rod 14. The distal end 15 of shaft 14 forms a connection with a first appendage 16 at joint 18. A second appendage 17 is spaced from the appendage 16 and shaft 17, and is generally parallel to appendage 16 at joint 18 and shaft 14 as shown in FIG. 3.

The appendage 16 is comprised of a pair of sections 24, 25 and an angle section 26 that forms a concavity as shown in FIG. 4. An angle 27 of about 70°–80° is formed between the appendage 16 sections 24 and 25 as shown in FIG. 4.

The appendage 17 has a free end 19. The appendage 17 has a pair of sections 21, 22 that are connected with curved section 20 that defines a concavity. An angle 23 is formed between the sections 21, 22 as shown in FIG. 2. The angle 23 can be about 70°–80°.

A transverse curved bridge section 28 forms a connection between the appendages 16, 17 as can be seen in FIGS. 2–5. The bridge section 28 is curved, providing a concave surface 29 that can engage suture during use.

Appendages 16, 17 are spaced apart to provide a slot 30 therebetween that communicates with the concave surface 29 and the curved sections 20 and 26. This allows the surgeon to insert a length of suture into the slot 30 by placing the suture adjacent free end 19 of appendage 17 and pulling the suture in between free end 19 and shaft 14 and towards distal end 13.

FIGS. 6–8 and 8A illustrate a loading of a suture 32 to instrument 10 and more particularly to the bridge section 28 thereof. FIGS. 9–14 illustrate a tying of a knot with suture to patient's bone tissue 31.

Figure 6:
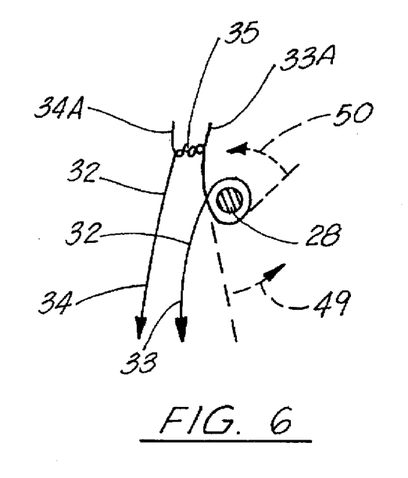
FIGS. 6–8 and 8A are schematic perspective views illustrating the wrapping of a length of suture three hundred sixty degrees (360°) about the instrument distal end portion.
Figures 7, 8A:
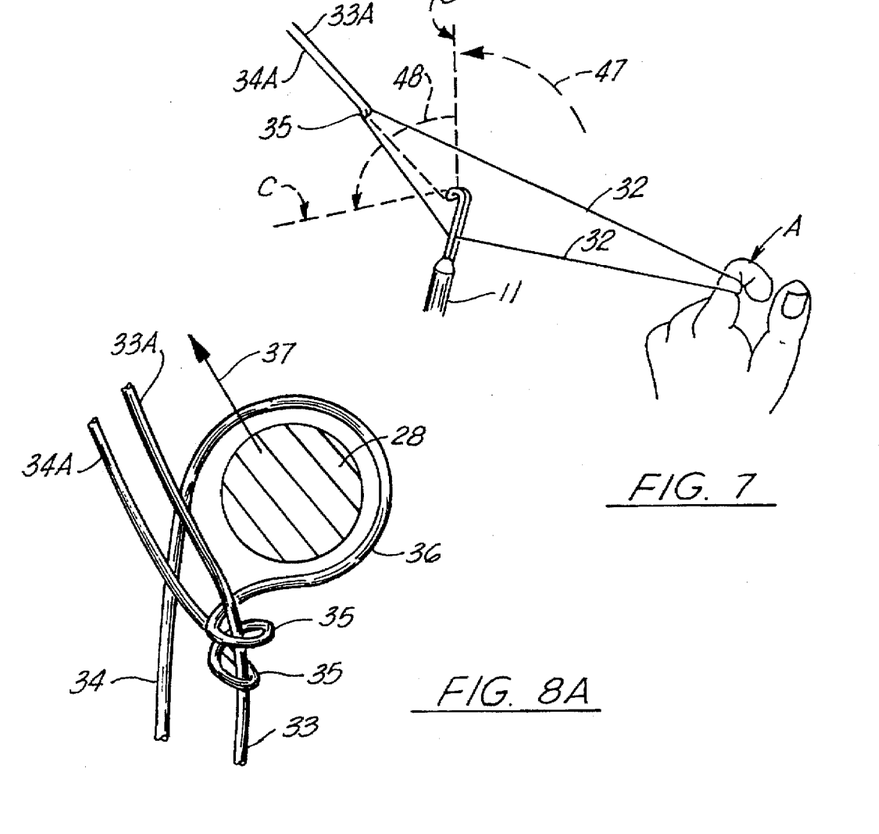

In FIGS. 6–7, the surgeon holds free end 33–34 with one hand (e.g. left hand) and holds the instrument 10 in the other (right) hand. The surgeon places one filament 33 into slot 30. The surgeon then moves his or her hand in sequence to positions A, B, then C while holding free ends 33–34 to load the suture.

The filaments 33A, 34A are engaging tissue (e.g. bone, ligaments, etc.). The position of filaments 33, 34 moves from A to B to C as shown in FIG. 7. In the "A" or starting position, the surgeon's hand and the filaments 33, 34 are shown. There are dotted lines that schematically indicate positions that the surgeon's hand and filaments 33, 34 occupy as loading progresses in positions B and C.

Figure 8:
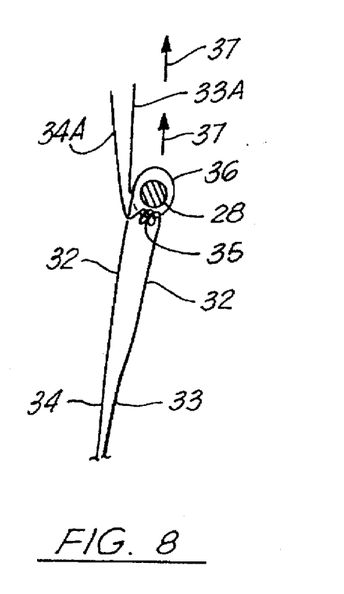

The path of the suture filament 33 wrapping about bridge 28 is shown by arrows 47–48 in FIG. 7 and by arrows 49, 50 in FIG. 6. FIGS. 8 and 8A show the complete loop 36 formed about bridge 28 so that the instrument 10 can pull the loop 36 in the direction of arrow 37 in FIGS. 8 and 8A to tighten the knot.

Figures 9, 10:
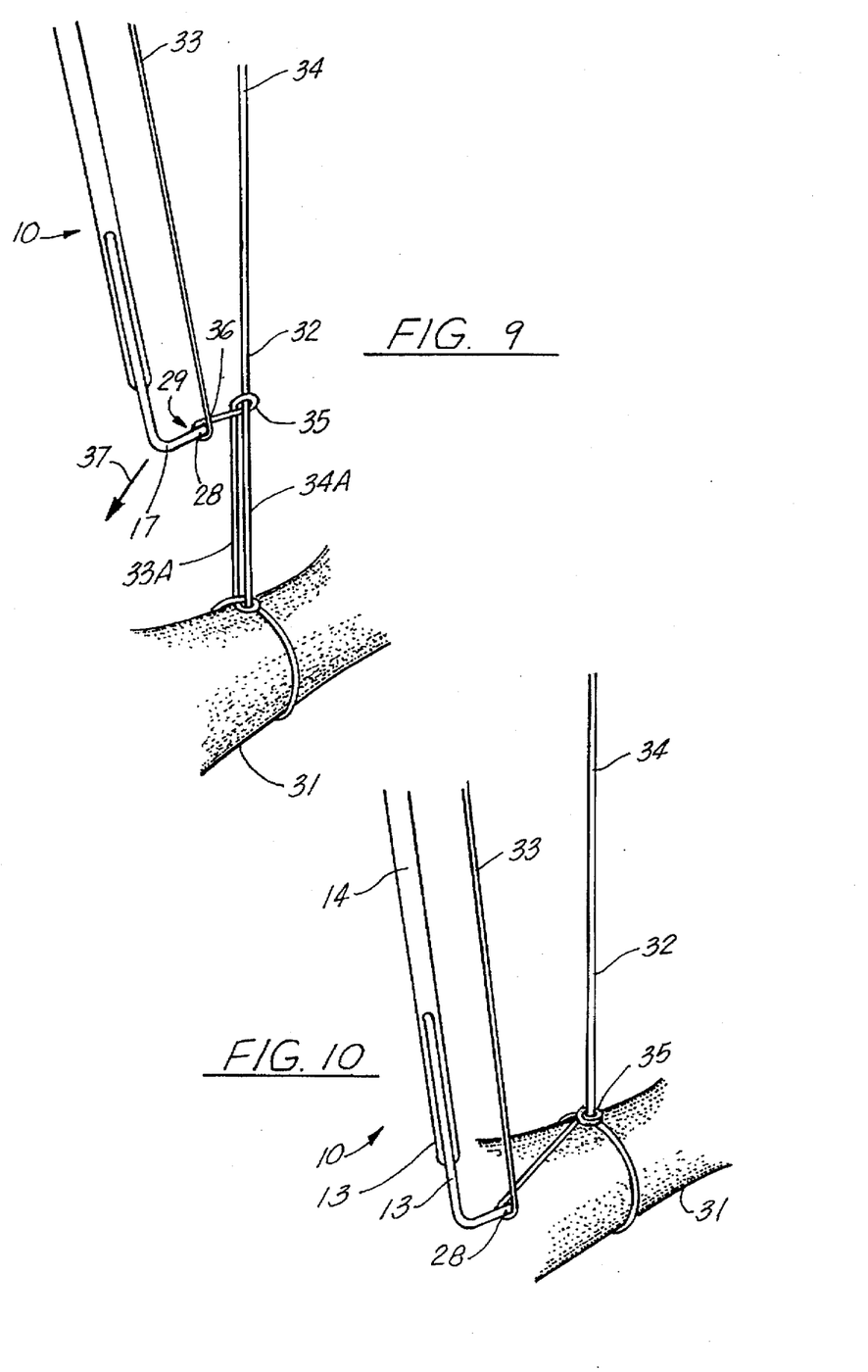
FIGS. 9 and 10 are schematic perspective sequential views illustrating the tying of a knot using the apparatus of the present invention.

FIGS. 9 and 10 show the apparatus 10 of the present invention being used to tie a length of suture 32 to selected patient's tissue such as bone tissue 31. The length of suture 32 has a pair of free ends 33, 34. A knot 35 has been preliminarily formed in FIG. 6. The surgeon places the instrument 10 on one free end 34 forming a loop 36 of the suture after connecting the suture to the bridge 28 section of instrument 10 wherein the length of suture 33 at the loop 36 engages the curved surface 29 as shown.

The surgeon completes the knot by pulling the instrument 10 in the direction of arrow 37 while holding the free end 34 with one hand. The surgeon grips the instrument handle 12 and free end 33 of the suture 32 with the other hand during this operation. In FIG. 10, the completed knot 35 is shown tightened against the patient's bone tissue 31.

Figures 11, 12:
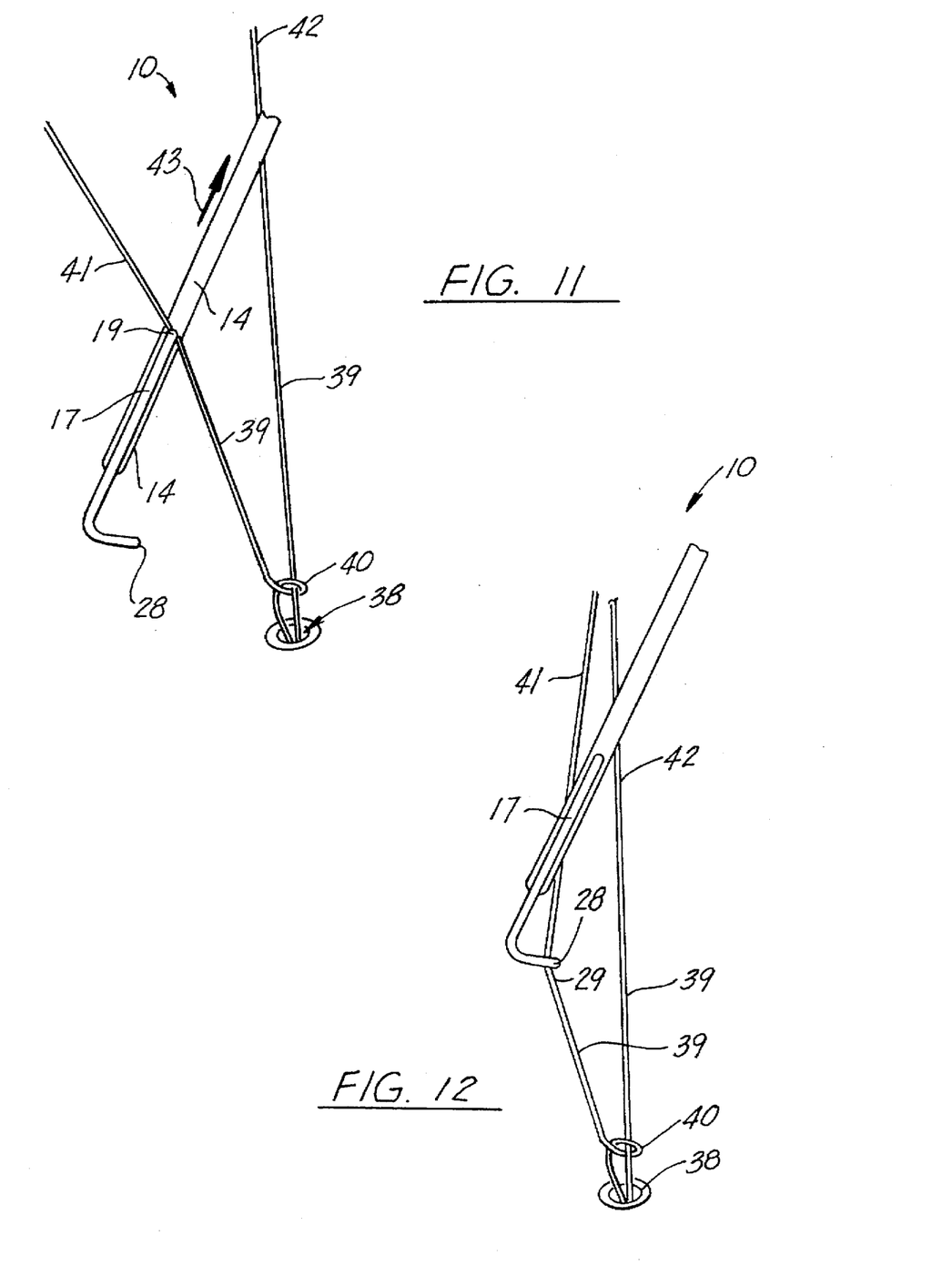
FIGS. 11–14 are perspective schematic sequential views illustrating the tying of a knot within a deep recess or body cavity.
Figure 13:
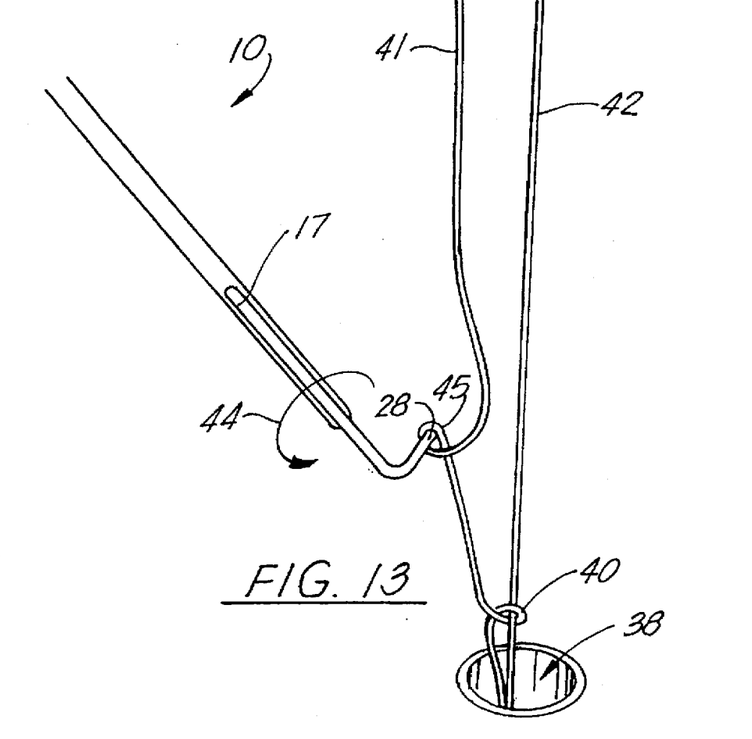
Figure 14:
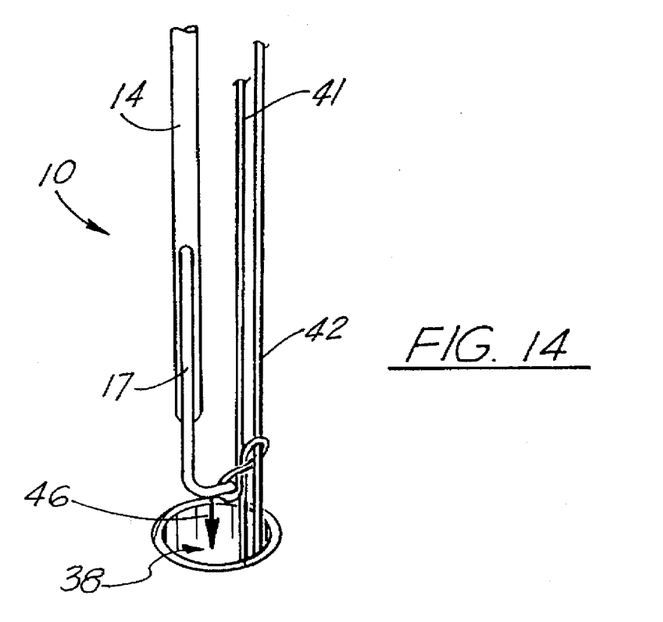

FIGS. 11–14 show sequentially the steps that the surgeon uses when tying a knot deep within a patient's body cavity. In FIGS. 8–11, a body cavity is schematically illustrated by the number 38. A length of suture 39 is shown having a preliminary knot 40 that has been loosely tied as shown in FIG. 8. The suture 39 has two free ends 41, 42. The surgeon places the instrument 10 on the free end 41 by positioning the suture end 41 preliminary between free end 19 of appendage 17 and instrument shaft 14 as shown. The surgeon then pulls up on the instrument 10 in the direction of arrow 43 in FIG. 8 so that the suture travels into the slot 30 and engages the curved surface 29 of bridge 28 as shown in FIG. 12. In FIG. 13, the surgeon rotates the instrument 10 in the direction of arrow 44 forming the loop 45 as shown. In FIG. 14, the knot is completed when the surgeon pushes the instrument 10 in the direction of arrow 46 thus pulling the loop 45 and knot 40 until they are tight.

The following table lists the parts numbers and parts descriptions as used herein and in the drawings attached hereto.

| PARTS LIST | |
|---|---|
| Part Number | Description |
| 10 | knot puller instrument |
| 11 | instrument body |
| 12 | handle |
| 13 | distal end portion |
| 14 | elongated shaft |
| 15 | lower end |
| 16 | appendage |
| 17 | appendage |
| 18 | joint |
| 19 | free end |
| 20 | curved section |
| 21 | section |
| 22 | section |
| 23 | angle |
| 24 | section |
| 25 | section |
| 26 | curved section |
| 27 | angle |
| 28 | bridge section |
| 29 | concave surface |
| 30 | slot |
| 31 | patient's tissue |
| 32 | length of suture |
| 33 | free end |
| 33A | filament |
| 34 | free end |
| 34A | filament |
| 35 | knot |
| 36 | loop |
| 37 | arrow |
| 38 | cavity |
| 39 | length of suture |
| 40 | knot |
| 41 | free end |
| 42 | free end |
| 43 | arrow |
| 44 | curved arrow |
| 45 | loop |
| 46 | arrow |
| 47 | arrow |
| 48 | arrow |
| 49 | arrow |
| 50 | arrow |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A knot puller instrument for use with surgical suture in tying surgical knots comprising:
   a) an elongated main body member formed of a rigid structural material that can be sterilized, said body having maximum thickness and proximal and distal end portions and being much longer than its thickness;
   b) the proximal end portion of the main body including a handle that can be gripped by a surgeon during use;
   c) the distal end of the main body having a pair of spaced apart appendages that are positioned to hold a length of suture therebetween, one of the appendages being a first appendage that is integrally connected to and an extension of the main body portion, the other appendage being a second appendage that is spaced therefrom and providing an unattached free end;
   d) said pair of appendages each including a hook portion that includes a concavity facing the instrument body;
   e) a transverse curved bridge connector that extends between the hook portions;
   f) a slot in between the appendages that defines a space for receiving and holding the length of suture; and
   g) the second appendage being connected to the bridge connector, entirely spaced away from the instrument body between the bridge connector and the free end portion of said appendage so that suture can be inserted into the slot at the free end portion of the appendage by placing the suture in between the free end portion and the instrument body and then moving the suture toward the curved bridge.

2. The surgical knot puller instrument of claim 1 wherein the main body has a generally uniform cross section and a linear central longitudinal axis.

3. The surgical knot puller instrument of claim 2 wherein each of the appendages has a straight section with a longitudinal axis.

4. The surgical knot puller instrument of claim 3 wherein each of the appendages has a straight section with a longitudinal axis that is parallel to the main body central longitudinal axis.

5. The surgical knot puller instrument of claim 1 wherein at least one of the appendages has a pair of sections that define therebetween an acute angle of between about 60 and 90 degrees.

6. The surgical knot puller instrument of claim 1 wherein the curved bridge connector and the hook portions of the appendages define a U-shaped portion for engaging a length of suture.

7. The surgical knot puller instrument of claim 1 wherein each of the appendages has a pair of sections that define therebetween an acute angle of between about 60 and 90 degrees.

8. The surgical knot puller instrument of claim 1 wherein the space between the appendages is between about 0.1 and 8.0 mm along a portion of the length of each appendage.

9. The surgical knot puller instrument of claim 1 wherein the free end is spaced from the instrument body by a measure of between 0.1 and 8.0 mm.

10. The surgical knot puller instrument of claim 1 wherein the bridge connector has a concave surface for engaging the suture that has a curvature of between about 1.0 and 15 mm.

11. A method of tying a surgical knot in an elongated length of suture that has first and second free end portions and a middle portion comprising the steps of:
   a) providing an elongated instrument body having proximal and distal end portions, the distal end having a pair of appendages with a slot therebetween, one appendage being a first appendage that is attached at one of its ends to the body, the other end of the first appendage having a bridge connector, the other appendage being a second appendage having a free end that is unattached from the body and spaced therefrom;
   b) inserting the length of suture in between the appendages into the sloot until it engages the bridge connector;
   c) routing the suture about a patient's tissue that is to be sutured so that the middle portion of the suture is placed next to the tissue to be sutured and the free end portions are extended away from the tissue to be sutured;
   d) forming a loose knot with the two free end portions, the knot being spaced from the tissue to be sutured;

e) wrapping the suture about the distal end portion of the instrument at a position on the suture in between a first free end and the tissue to be sutured thereby forming a loop about the instrument distal end portion;

f) applying tension to the second free end portion of the suture;

g) pulling the loop toward the tissue to be sutured; and h) applying tension to the loop with the instrument until the loose knot is tightened.

12. The method of claim 11 wherein the instrument in step "a" has a hook portion and in step "d" the suture is wrapped about the hook portion.

13. The method of claim 11 wherein step "a" comprises the step of providing an elongated instrument having proximal and distal end portions, the distal end portion having an appendage with a slot positioned in between the appendage and the instrument shaft and further comprising the step between steps "c" and "d" of placing the suture in the slot.

14. The method of claim 11 wherein the loop in step "d" is wrapped about 360 degrees about the instrument to form the loop.

15. The method of claim 11 wherein the loop in step "f" is pulled by allowing suture to continuously pass the instrument body and the instrument distal end and the loop move toward the tissue to be sutured.

* * * * *